United States Patent [19]

Kalisch et al.

[11] 4,331,920

[45] May 25, 1982

[54] MAGNETIC OR MAGNETO-INDUCTIVE MATERIALS TESTER WITH IMPROVED PROCESSING CIRCUIT

[75] Inventors: Alfons Kalisch, Reutlingen; Günther Stritzke, Gomaringen, both of Fed. Rep. of Germany

[73] Assignee: Institut Dr. Friedrich Förster Prüfgerätebau, Fed. Rep. of Germany

[21] Appl. No.: 46,547

[22] Filed: Jun. 7, 1979

[30] Foreign Application Priority Data

Jun. 14, 1978 [DE] Fed. Rep. of Germany ....... 2825958

[51] Int. Cl.³ .................... G01N 27/72; G01R 33/12; H03K 17/00; H03B 1/00
[52] U.S. Cl. .................................. 324/225; 324/233; 328/150; 328/162
[58] Field of Search .............. 324/225, 233, 234, 236; 331/65, 143, 177 R; 330/9; 328/162, 165, 127, 128, 150

[56] References Cited

U.S. PATENT DOCUMENTS

| | | | |
|---|---|---|---|
| 3,550,018 | 12/1970 | James et al. | 328/127 |
| 3,824,481 | 7/1974 | Sponholz et al. | 328/162 |
| 3,842,371 | 10/1974 | Kelley | 331/143 |

Primary Examiner—Gerard R. Strecker
Assistant Examiner—Walter E. Snow
Attorney, Agent, or Firm—George J. Netter

[57] ABSTRACT

A magneto-inductive materials tester has probes which, when brought into contact with the material, produce an electrical signal corresponding to properties of the material desired to be tested. Apparatus for evaluating this test signal has at least one device for producing a compensation voltage to eliminate residual or drift error voltages that may be superimposed on the test signal. The compensating device includes a counting pulse generator, at least one pulse counter connected to the generator at least temporarily, and a digital/analog converter connected to the pulse counter output to provide the desired compensation voltage.

5 Claims, 11 Drawing Figures

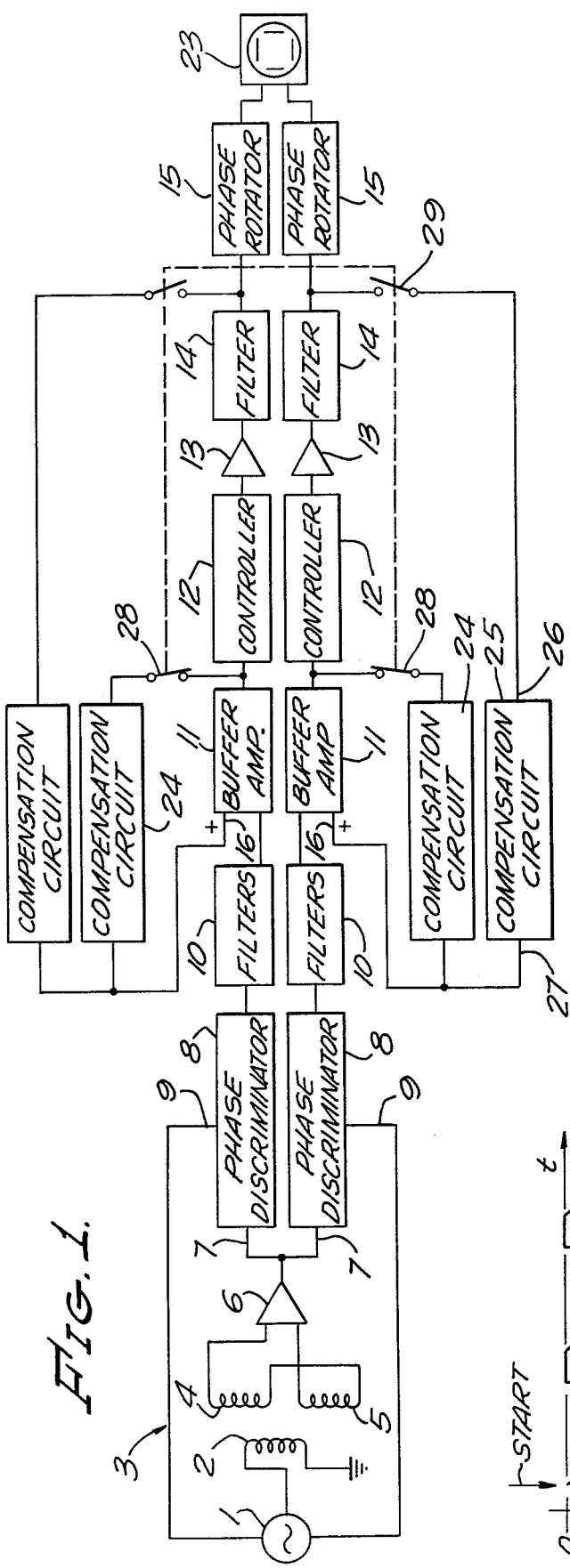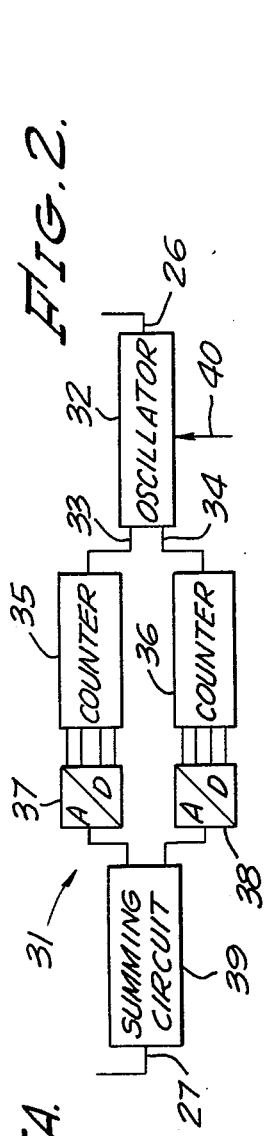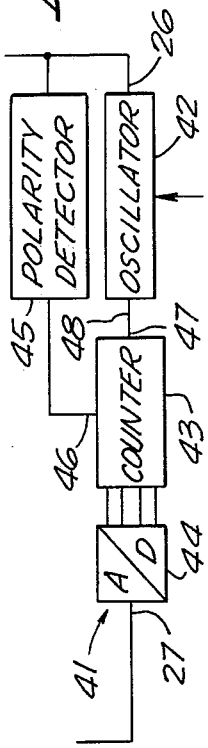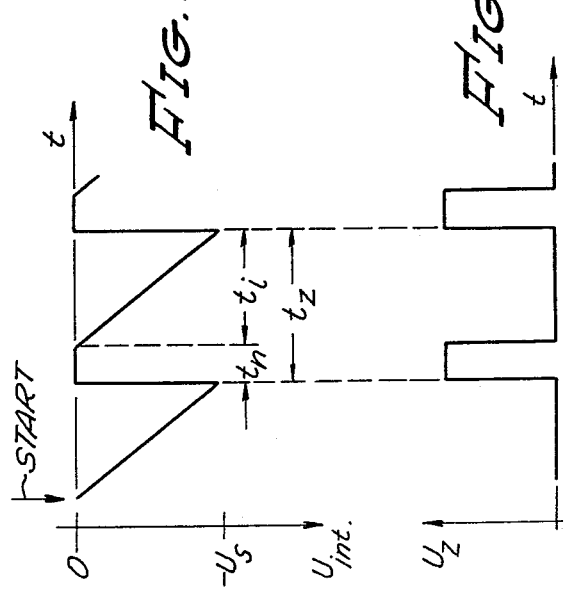

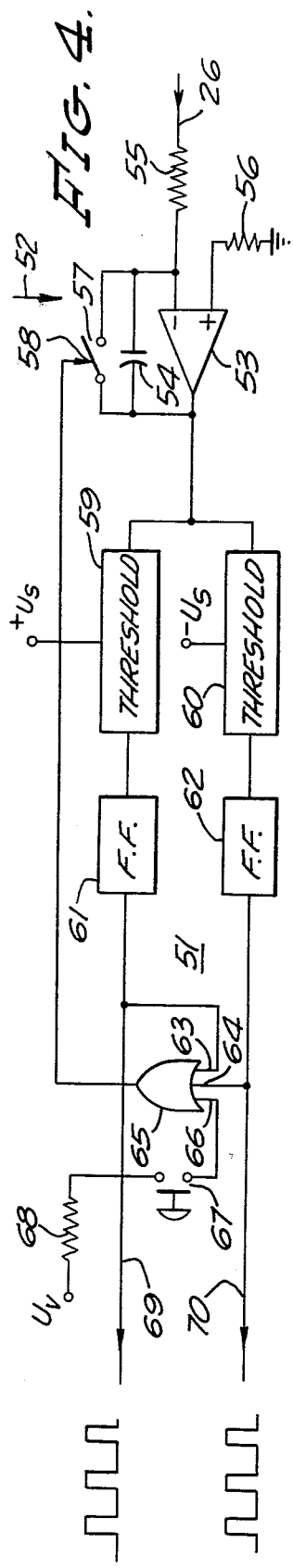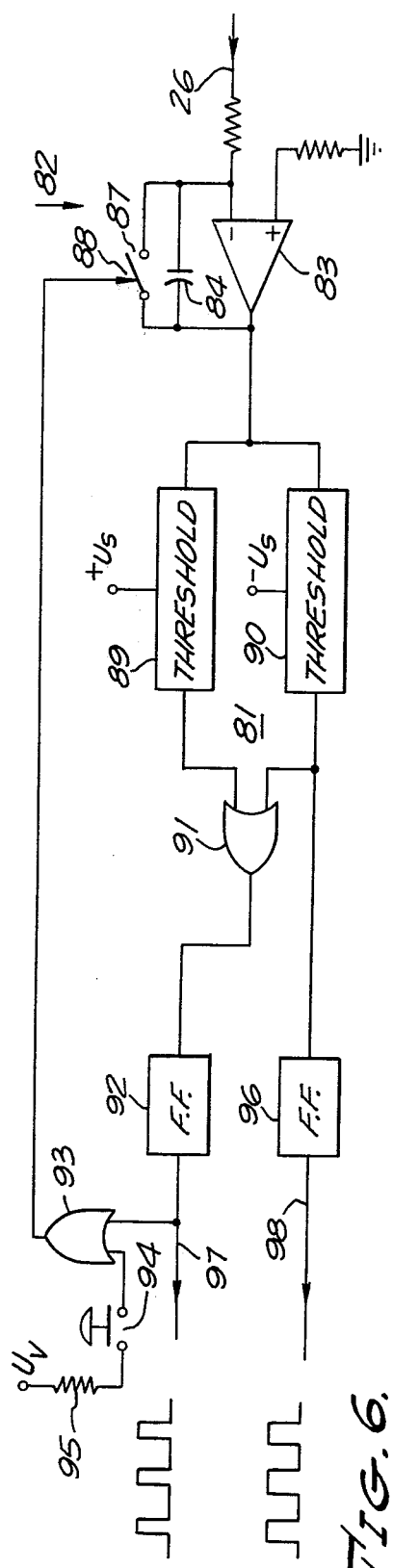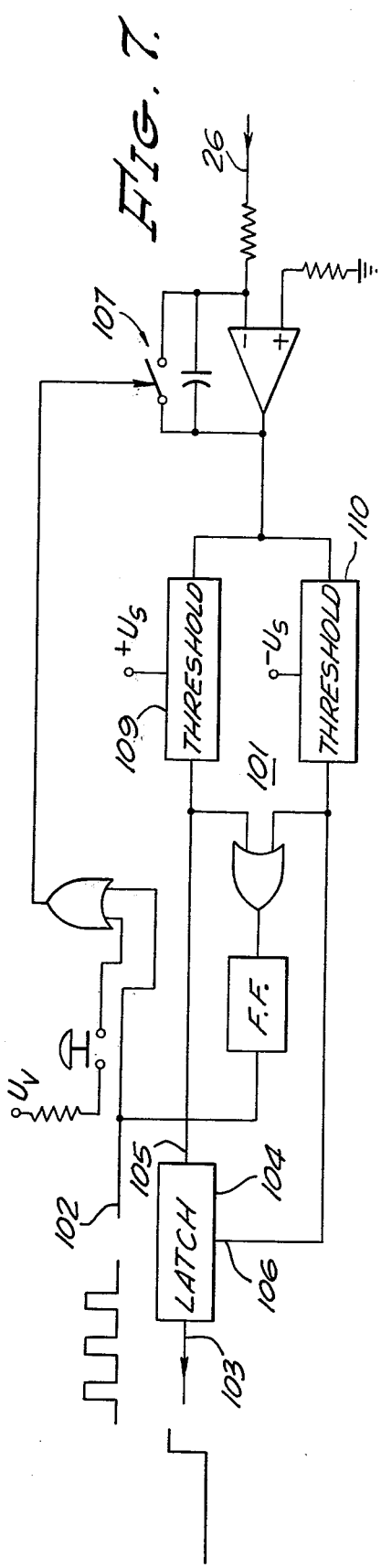

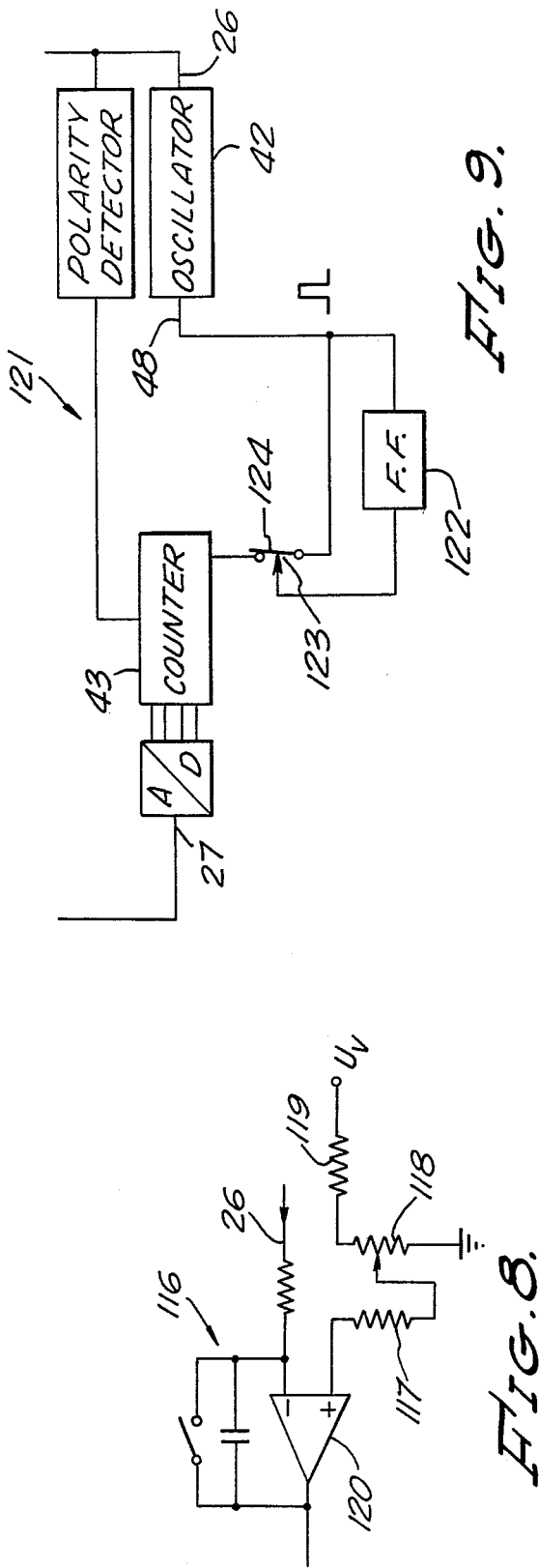
Fig. 9.
Fig. 8.
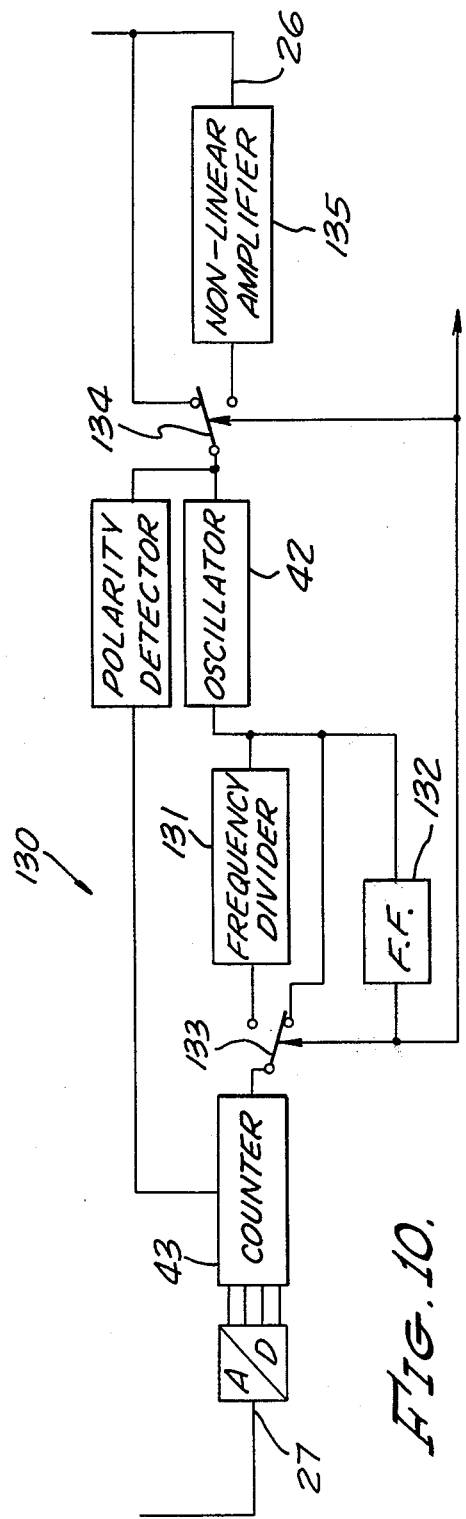
Fig. 10.

MAGNETIC OR MAGNETO-INDUCTIVE MATERIALS TESTER WITH IMPROVED PROCESSING CIRCUIT

FIELD OF THE INVENTION

This invention relates to a magnetic or magneto-inductive materials tester with probes which, when brought into contact with the material, produce an electrical signal corresponding to certain properties of the material desired to be tested. Apparatus for evaluating this test signal has at least one compensating device which produces a compensation voltage to eliminate residual or drift error voltages that may be superimposed on the test signal. The compensating device includes a counting pulse generator, at least one pulse counter connected to the generator at least temporarily, and a digital/analog converter connected to the pulse counter output to provide the desired compensation voltage.

PRIOR ART

A known tester is that disclosed in U.S. Pat. No. 4,006,407, having a fixed-frequency counting pulse generator, the counting pulses of which can be applied to the counting input of a pulse counter by actuating a pushbutton. A digital/analog converter is connected to the counter output and the output of the converter is connected to one input of a comparator. The voltage to be compensated is presented to another input of the compensator and the output signal of the comparator is fed to the counting direction input of the pulse counter. When counting pulses are fed to the pulse counter by operating the pushbutton, a counting process begins and the accumulated digital count is converted to a corresponding analog voltage at the output of the converter. As soon as the analog voltage attains a value slightly exceeding the voltage to be compensated, the output signal of the comparator reverses the counting direction of the pulse counter and the analog voltage at the converter output is reduced again. This continues until the voltage value is again below the value of the voltage to be compensated and counting is resumed in the original direction. In this manner a compensation voltage which varies around the given reference value is produced at the output of the converter for as long as the pushbutton is operated. The residual voltages to be compensated by operation of the pushbutton can have various causes, e.g., inadequate symmetry of the probe system, and can often reach considerable magnitudes. It is necessary in the patented apparatus, therefore, if the compensation process is not to be too slow, for the speed of compensation, i.e., the counting frequency, to be set very high.

Although the digital storage used for compensation in this known tester possesses the advantage of unlimited storage time compared with, say, capacitive storage in common use formerly, the tester involves some serious shortcomings. The compensation device also only permits very coarse compensation.

If the compensation voltage obtained is only used to produce a zero signal by differencing with the voltage to be compensated, the approximation to the required zero signal after the subsequent amplifier stages will be inadequate unless additional, possibly manual, compensation takes place. However, if the amplifier stages of the tester, or some of them, are included in the compensation, i.e., the compensation voltage obtained is used to produce the zero signal condition at a place of higher signal level, at the necessarily high control rate and with the unavoidable time constants of the amplifier stages, there will be considerable and undesirable overshoot of the compensation voltage. The hunting of the compensation voltage described above means that it depends on the chance instant of releasing the pushbutton as to whether overcompensation or undercompensation results. Both can assume high values as already explained.

Another disadvantage is that the sensitivity controller of the tester described is placed before the compensating device. The result of this is that compensation must be carried out again after each change in sensitivity setting because the stored digital value is interrelated to a specific sensitivity setting. Incorporating the sensitivity controller in the comparator would increase the dynamic range and result in a corresponding increase in the time constants, thus increasing the compensation voltage overshoot still more.

Another disadvantage of the tester described is that it is only possible to change over the manually operated pushbutton-triggered compensation to continuous compensation of the slow drift voltage if the digital storage is dispensed with in favor of the former capacitive storage technique. On the other hand, however, the compensation of drift voltage also requires the use of capacitors having a relatively long storage time if absolute-value transmitters are employed and extended interruptions between successive measurements can be expected.

OBJECTS AND SUMMARY OF THE INVENTION

An object of the present invention is to provide a materials tester having a compensating device exhibiting relatively large storage time constants without serious overshoot of the compensation voltage and also without thereby extending the time for achieving compensation excessively.

The present invention offers a favorable compromise between divergent requirements and enables the control rate of the compensation to adapt automatically to the magnitude of the voltage to be compensated.

High residual voltages give rise to a high voltage-sensitive oscillator frequency and therefore to a high control rate. The counting oscillator frequency, and therefore also the control rate, decreases as the compensation progresses such that overshoot of the compensation voltage need also not be feared when the compensation apparatus uses a number of different stages, such as amplifiers, filters, sensitivity controllers (i.e., when the compensation voltage fed to the input of these stages is used to produce zero output signal condition). A relatively high dynamic range can be covered and undesirable hunting of the compensation voltage is eliminated completely. Changeover to continuous compensation of the drift voltage is enabled without difficulty.

In an advantageous form of the invention a voltage-sensitive oscillator is used which incorporates an integrator having the voltage to be compensated as one input and which integrates each time a given threshold voltage is reached. Thus, the time taken to reach the threshold voltage, and therefore the frequency of the oscillator, depends on the magnitude of the voltage to be compensated.

In another form of the invention the compensation process is terminated by time comparison when the period of the oscillator voltage has exceeded a preset time value. This allows the degree of compensation, i.e, the degree of approximation to the required compensation target, to be preselected with great precision.

DESCRIPTION OF THE DRAWING

FIG. 1 is a function block diagram of the materials tester of this invention.

FIGS. 2 and 3 depict alternative versions of compensating circuits for use in the tester.

FIG. 4 is a voltage-sensitive oscillator.

FIGS. 5a and 5b show the threshold and counting pulse output, respectively, from the compensation circuit.

FIGS. 6 and 7 are alternative voltage-sensitive oscillators.

FIG. 8 shows an alternative input circuit for use with the oscillators.

FIGS. 9 and 10 depict compensating devices with time comparison.

DESCRIPTION OF PREFERRED EMBODIMENTS

FIG. 1 shows a materials tester which, together with the compensating devices illustrated in detail in the other figures, forms the subject of this invention. Although the invention can also employ a magnetic tester, such as an alternating-field leakage-flux tester, in the illustrative description here a magneto-inductive tester (i.e., eddy-current tester with XY display of the test signal) has been selected.

With reference particularly to FIG. 1, an alternating current generator 1 feeds the excitation coil 2 of the probe system 3 whose difference-connected receiver coils 4 and 5 are connected to the input of an amplifier 6. The output of amplifier 6 is applied to the signal inputs 7 of two phase discriminators 8. From generator 1 two signals 90° out of phase are fed to control inputs 9 of the phase discriminators 8. The X and Y output signals of the two phase discriminators 8, which are each proportional to the two vertically-stacked X and Y components of the test signal from coils 4, 5, are smoothed by low-pass filters 10 after which they pass along two channels via buffer stage 11, sensitivity controller 12, amplifier 13, rate matching filter 14 and phase-rotation units 15 to the X and Y inputs of a cathode-ray oscilloscope 23. For each of the two channels X and Y there are two, basically identical, compensating circuits 24, 25 each having an input 26 and an output 27, the latter being connected to a summation input 16 of buffer stage 11. The compensating circuits 24, 25 operate to produce a compensation voltage at their respective outputs 27 responsive to the voltage at their input 26 and increase until a predetermined reference value, usually zero or nearly zero, is attained at input 26. The compensation process is initiated by a command which is generally issued simultaneously for the X and Y channels. Two switches 28, 29 are linked together and to the corresponding switches of the other channel for simultaneous operation. Their position determines that either compensating device 24 is connected for a first and coarse compensation, or compensating device 25 is interconnected providing a subsequent and fine compensation. Whereas in the first case input 26 and output 27 of the compensating device 24 are at the same amplification level, in the latter case the input and output levels are separated by the sensitivity controller 12, amplifier 13 and filter 14.

Turning now to FIG. 2, a first form of compensating circuit 31 is shown. A voltage-sensitive oscillator 32, whose input 26 is also the input for the compensating device 31, possesses two outputs 33, 34 and a start signal terminal 40. Triggered into operation by a signal applied to 40, oscillator 32 runs at a frequency depending on the magnitude of the voltage at input 26. The oscillator pulses appear at either output 33 or 34 according to whether the voltage at input 26 is positive or negative. A counter 35, 36 with a digital/analog converter 37, 38 in series is connected to each of the two outputs 33, 34. The outputs of the two converters are fed via a summing stage 39 to the common output 27. Depending on the polarity of the voltage at input 26, therefore, either counting pulses from output 33 are fed to counter 35 or from output 34 to counter 36 and the results are converted into an analog voltage in converter 37, 38. The two converters 37, 38 are designed to give voltages of different polarity. A high input voltage means a high counting frequency and rapid increase in the compensation voltage at output 27. Conversely, as compensation progresses, i.e., as the voltage at input 26 becomes smaller, the frequency decreases, and therefore also the rate of change of the compensation voltage.

FIG. 3 shows an alternate form of compensating circuit 41 with a voltage-sensitive oscillator 42 and a reversible counter 43, having its counting input 47 connected to the oscillator output 48. A digital/analog converter 44 receives the accumulated count of the counter. The voltage whose value determines the oscillator frequency is again presented to terminals 26 of oscillator 42. The voltage-sensitive oscillator 42 incorporates a supplementary unit 45 which gives a binary signal dependent on the polarity of the voltage at input 26. This signal is fed to the counting direction input 46 of the counter 43 and determines whether the counter counts forward or backward. The remainder of the mode of operation is identical to that of the FIG. 2 circuit.

FIG. 4 shows a detailed function block circuit of a voltage-sensitive oscillator 51 which could be used in the compensation circuit of FIG. 2. The heart of the oscillator 51 is an integrator 52 including a computing amplifier 53, a capacitor 54 linking the amplifier output to its inverting input and two resistors 55, 56 connected to the two inputs. The free end of resistor 55 is also input 26 for the voltage-sensitive oscillator 51, whereas resistor 56 is maintained at zero potential. Capacitor 54 is bridged by a switch 57, e.g., a field-effect transistor, which can be operated by a signal applied to its control input 58. The output of the computing amplifier 53 is fed into the inputs of two threshold stages 59, 60 which respond, respectively, to a signal exceeding a prescribed positive value, or falling below a predetermined negative value, identified as $U_s$, and give a corresponding binary signal at their outputs. Two monostable flip-flops 61, 62 are connected to the threshold stages and, in turn, are connected to the inputs 63, 64 of an OR-gate 65. A third OR-gate input 66 is connected via a pushbutton contact 67 and a resistor 68 to a supply voltage source $U_v$. The OR-gate 65 provides a control signal input 58 of the switch 57. The two flip-flops 61, 62 drive the two counters 35, 36 in FIG. 2 via leads 69, 70.

As to operation of the oscillator 51 in FIG. 4, momentary operation of the pushbutton 67 closes switch 57 temporarily via the OR-gate 65 and the capacitor 54 discharges. Immediately on the switch 57 opening, linear charging of the capacitor 54 begins with a rate of increase depending on the magnitude of the voltage at 26. As soon as the output voltage of the amplifier 53 attains the threshold value of one of the two threshold stages, depending on the polarity of the voltage at 26, one of the threshold stages 59 or 60 is energized providing a driving signal to the corresponding flip-flop 61 or 62, as the case may be. This passes on the signal via OR-gate 65 to control 58 of the switch 57 resetting it when the predetermined delay time ($t_n$) has elapsed. The capacitor 54 can discharge completely during the delay time $t_n$ and a new charging cycle begins thereafter. When the integrator 52 exhibits good linearity the charging or integrating time $t_i$ is inversely proportional to the voltage at input 26 of the integrator, and the frequency of repetition of charging, i.e., the oscillator frequency, is approximately proportional to the input voltage at 26.

FIG. 5a shows a pulse diagram of the output voltage of the integrator 52 with ramp-form pulses whose period $t_z$ consists of the sum of integrating time $t_i$ and the delay time $t_n$. FIG. 5b shows a pulse diagram of the counting pulses on leads 69, 70 whose pulse width corresponds to the delay time $t_n$, and the period equals the period $t_z$ of the ramp pulses. Depending on the polarity of the voltage at input 26 counting pulses are produced on lead 69 or 70 and actuate counter 35 or 36. These produce the compensation voltage at output 27 in the manner described above.

FIG. 6 illustrates an alternate form of voltage-sensitive oscillator 81 which can be used in the compensating device 41 of FIG. 3. It utilizes an integrator 82 and a computing amplifier 83 together with threshold stages 89, 90 of the same construction and operation as in the FIG. 4 embodiment. The outputs of the threshold stages 89, 90 are connected via an OR-gate 91 to a monostable flip-flop 92, the latter having a delay time of $t_n$. The output of the flip-flop 92 is connected to a further OR-gate 93 which also has the supply voltage $U_v$ as another input under the control of a pushbutton 94 and a series resistor 95. The output gate 93 is connected to the control input 88 of switch 87, which on closing discharges the capacitor 84 of the integrator 82 in the manner described earlier. Connected to the output of the threshold stage 90 is a monostable flip-flop 96, the delay time $t_m$ of which is greater than the delay time $t_n$. The output of the flip-flop 92 is connected via a lead 97 to the counting input 47 of the counter 43 in FIG. 3, whereas the output of the flip-flop 96 via lead 98 is connected to the counting direction input 46 of the counter 43.

With respect to operation of the voltage-sensitive oscillator 81, actuation of the pushbutton 94 closes the switch 87 temporarily via gate 93 and discharges capacitor 84. This begins the alternate charging and discharging of the capacitor 84 already described above in connection with the circuit of FIG. 4. Opening the switch 87 starts the charging process and on attaining the prescribed value of the threshold stages 89 or 90, charging is terminated via the OR-gate 91, flip-flop 92, OR-gate 93 and switch 87. The counting pulses available on lead 97 are illustrated in FIG. 5b and the pulse frequency is proportional to the voltage at input 26. Counter 43 (FIG. 3) accumulates counting pulses at its input 47; the counting direction, i.e., forwards to backwards, is determined by the signal at the counting direction input 46. However, pulses of width $t_m$ only occur at 46 when the voltage at input 26 is of a specific polarity. To insure that the pulses at the counting direction input 43 cover the counting pulses, $t_m$ is made greater than $t_n$.

A still further version of voltage-sensitive oscillator 101 is that shown in FIG. 7 which is similar in many respects to the oscillator 81 in FIG. 6, and reference to the description of operation of that circuit is hereby made. The counting pulses on lead 102, which are fed to the counting input 47 in FIG. 3, are obtained in the described manner by means of integrator 107, however, an alternative method is used for producing the counting direction signal on lead 103. Connected to the outputs of the two threshold circuits 109, 110, which correspond to the threshold stages 89, 90 in FIG. 6, is a bistable flip-flop 104, sometimes referred to as a "latch", having the characteristic that the signal on lead 103 can only be changed by a signal at the input from which the output signal does not originate. In other words, if the flip-flop 104 has been set by a signal at input 105 it can only be reset by a further signal applied at input 106. Consequently, at output 103 there is a continuous signal, the character of which depends on whether counting pulses are present at the output of threshold stage 109 or 110, i.e., whether there is a positive or negative voltage at input 26.

In the previous examples it was assumed that the voltage at input 26 of the compensating device needed to be compensated to zero. However, it is also possible that this value should be other than zero. This is the case, for example, with the quality sorting of test specimens when a reference point is used which does not lie in the center of the oscilloscope screen 23. This result is easy to achieve by using an integrator 116 and amplifier 120 as shown in FIG. 8 having a selectively variable potential at its non-inverting input. For this purpose the input resistor 117 is connected to the slider of a potentiometer 118, one end of which potentiometer is connected to the supply voltage $U_v$ via a resistor 119 and the other end to ground. If such an integrator input is provided for the X and Y channels the potentiometers 118 can be used to adjust the reference point to any position on the screen.

The compensating device 121 shown in FIG. 9 differs from the similar device 41 shown in FIG. 3 through the provision of time comparison the function of which, after adequate approximation of the compensation to its reference value is achieved, is to switch off the latter. A retriggerable monostable flip-flop 122 is used which is connected to output 48 of the voltage-sensitive oscillator 41, and which is applied to the control input 123 of a switch 124 in the line between the oscillator 42 and counter 43. As long as the switch 124 is closed compensation is performed in the manner described above. The counting pulses permit retriggering of the flip-flop 122 at each period before its delay time has elapsed so that the flip-flop remains set continously and its output signal holds the switch 124 in the closed position. If compensation is so far advanced that the period $t_z$ of the counting frequency has become greater than the preset delay time $t_v$ for flip-flop 122, the latter resets and switch 124 isolates the counting pulses from counter 43 terminating compensation. The time comparison described can also be used to change over from coarse compensation to fine compensation as soon as the relevant preset criteria are available, i.e., as soon as the repetitive frequency of the counting pulses has become sufficiently low.

FIG. 10 illustrates a further use of the signal obtained by the time comparison, namely, to change over to continuous compensation as soon as compensation initiated by actuating a pushbutton has come sufficiently close to its reference value. The object of such continuous compensation is to eliminate small drift voltages which change very slowly. This task is very different from the previous requirement of compensating high residual voltages very rapidly. Therefore, other means are necessary for providing the continuous compensation. It is especially necessary to reduce the frequency of the counting pulses sufficiently so that the relatively rapid working signals cannot be compensated out. This is done in the compensating circuit 130 shown in FIG. 10 by a frequency divider 131 which is inserted between oscillator 42 and counter 43 by a retriggerable monostable flip-flop 132 and a switch 133 when the time criterion has been attained. Since the rates of change of drift voltage can differ widely, it is advisable for the frequency divider to have an adjustable dividing ratio. When the time criterion has been attained, an additional non-linear amplifier 135 is inserted before the input of the voltage-sensitive oscillator 42 by the signal from the flip-flop 132 and another switch 134. The amplifier 135 has a characteristic of initially increasing amplification and subsequently changing to saturation. This insures that the required frequency is reached quickly but not exceeded.

I claim:

1. In a material tester having probes which, when brought into contact with the material, produce an electrical signal corresponding to certain predetermined properties of the material, means for evaluating the signal of the probes and a compensating circuit which produces a compensation voltage to eliminate certain error voltages superimposed on the signal of the probes, said compensating circuit including a voltage-sensitive oscillator driven by the error voltages and providing a signal of a frequency functionally related to the magnitude of the error voltages, a pulse counter connected to the oscillator, a digital/analog converter connected to the pulse counter and the output of said converter providing the compensation voltage to the means for evaluating, the improvement comprising:
   electrically responsive switch means serially interconnected between the voltage-sensitive oscillator and the counter; and
   a time delay means driven by said oscillator and having a predetermined delay time, the output of said time delay means being connected to said switch means to interrupt counting when the delay time is exceeded by the pulse repetition period of the oscillator voltage.

2. A material tester as in claim 1, in which said time delay means is a retriggerable monostable flip-flop.

3. A material tester as in claim 1, in which said switch means on being interrupted serially interconnects a frequency divider between the voltage-sensitive oscillator and the counter thereby producing compensation at a different rate.

4. A material tester as in claim 3, in which the dividing ratio of the frequency divider is adjustable over a predetermined range.

5. A material tester as in claim 3, in which a further switch means simultaneously actuatable with said first recited switch means serially interconnects a non-linear preamplifier between the voltage-sensitive oscillator and the signal to be compensated during compensation at the different rate.

* * * * *